United States Patent [19]
Layzell et al.

[11] Patent Number: 5,965,801
[45] Date of Patent: Oct. 12, 1999

[54] APPARATUS FOR RAPID MEASUREMENT OF HYDROGEN CONCENTRATION AND ITS USE IN THE MEASUREMENT OF NITROGENASE ACTIVITY

[75] Inventors: David B. Layzell; Stephen Hunt; Adrian N. Dowling; Lawrence J. Winship; Zhongmin Dong, all of Kingston, Canada

[73] Assignee: Queen's University at Kingston, Kingston, Canada

[21] Appl. No.: 08/672,229

[22] Filed: Jul. 5, 1996

Related U.S. Application Data

[63] Continuation-in-part of application No. 08/324,646, Nov. 21, 1994, abandoned, which is a continuation-in-part of application No. 08/027,513, Mar. 4, 1993, abandoned.

[51] Int. Cl.$^6$ .............................. G01N 7/18; C12Q 1/25
[52] U.S. Cl. .................... 73/23.2; 73/863.41; 435/4; 435/287.5
[58] Field of Search ................. 72/23.2, 16, 863.41, 72/863.51, 864.81; 435/4, 287.5

[56] References Cited

U.S. PATENT DOCUMENTS

| 5,096,294 | 3/1992 | Layzell et al. | 356/326 |
| 5,302,268 | 4/1994 | Layzell et al. | 204/228 |

Primary Examiner—Michael Brock
Attorney, Agent, or Firm—Richard J. Hicks

[57] ABSTRACT

A method and apparatus for rapidly measuring nitrogenase activity of a nitrogen fixing plant growing in a medium in a non-porous container, is described. Gas containing hydrogen is sampled at the surface of the medium at a rate approximately equal to the rate of hydrogen diffusion from the medium, and the sample is passed to a hydrogen sensor where it is measured and nitrogenase activity is determined therefrom.

11 Claims, 8 Drawing Sheets

APPARATUS FOR RAPID MEASUREMENT OF HYDROGEN CONCENTRATION AND ITS USE IN THE MEASUREMENT OF NITROGENASE ACTIVITY

CROSS REFERENCE TO RELATED APPLICATIONS

This application is a continuation in part of U.S. patent application Ser. No. 08/324,646 filed Nov. 21, 1994 and now abandoned, which in turn is a continuation in part of application Ser. No. 08/027,513 filed Mar. 4, 1993 and now abandoned.

FIELD OF INVENTION

The invention relates to an instrument for measuring $H_2$ concentration in a gas stream, and the use of this instrument to measure nitrogenase activity in $N_2$ fixing organisms grown in pots. The instrument differs from previous apparatus developed for these purposes in that it does not require that the plants be sealed in their growth pots for gas exchange measurements, but allows these measurements to be made by sampling $H_2$ (a by-product of $N_2$ fixation) directly from the medium in which the plants are grown. This allows for very rapid measurements of nitrogenase activity involving little or no manipulation of the plant material being studied. As a result, large populations of plants may be screened quickly for variations in nitrogenase activity. This instrument would be especially useful for assessing variations in nitrogenase activity caused by application of different environmental treatments to a specific legume-rhizobium symbiosis.

BACKGROUND OF INVENTION AND PRIOR ART

The yield of many crop species is limited by the amount of nitrogen available in the soil, since nitrogen is a nutrient required for the synthesis of amino acids, proteins and other nitrogenous compounds such as DNA. To alleviate this limitation, farmers supplement the soil with nitrogenous fertilizers which are expensive and hazardous to the environment. Some important crop species such as the legumes soybean, pea, alfalfa, clover and bean, do not rely entirely on soil nitrogen but are able to meet their requirements by reducing atmospheric $N_2$ to ammonia. This process is called $N_2$ fixation and it is carried out by bacteria which form a symbiotic association with the roots of the host plant. The bacteria inhabit outgrowths of the root, termed nodules, which provide them with a suitable environment for $N_2$ fixation. Biological $N_2$ fixation is likely to become an essential component of sustainable agricultural systems, and a great deal of research is currently in progress to investigate the genetics of nodule formation and to determine the factors which regulate $N_2$ fixation in leguminous crops. Consequently, a simple, accurate method is required for providing a non-invasive measurement of the rate of $N_2$ fixation.

The reduction of atmospheric $N_2$ to ammonia is catalyzed by the enzyme nitrogenase and the activity of this enzyme therefore determines the $N_2$ fixation rate. Several methods have been devised to measure the $N_2$ fixation rate and/or nitrogenase activity of legumes. These methods include:

(a) Measurement of whole plant nitrogen increment in which plants are harvested at different times during development and their nitrogen content measured. This method is destructive, labour intensive, requires complex and expensive equipment and does not distinguish between the nitrogen derived from the soil and that derived from $N_2$ fixation.

(b) Measurement of the $^{15}N$ and $^{14}N$ content of plant tissues and comparison of this with that of the atmosphere and the soil (the $^{15}N$ natural abundance assay). Alternatively, nodulated roots may be fed with an atmosphere enriched in $^{15}N_2$ ($^{15}N_2$ enrichment assay) or a soil enriched in $^{15}NO_3^-$ or $^{15}NH_4^+$ ($^{15}N$ dilution assay) and the subsequent rate of $^{15}N$ incorporation into tissues measured. These assays are destructive, time-consuming and require the use of expensive and complex analytical instruments. Also, like the nitrogen-increment method, they provide only a time-integrated measurement of nitrogen incorporation and do not show how nitrogenase activity and $N_2$ fixation rate may vary over the short term.

(c) An acetylene reduction assay in which the nodulated roots of the legume are supplied with a gas containing about 10% acetylene and the reduction of this acetylene to ethylene is monitored with time. In the presence of 10% acetylene, virtually all electron flow through nitrogenase is diverted to acetylene reduction to ethylene. Therefore, the rate of ethylene production provides a measure of total nitrogenase activity. The assay can be performed by sealing the nodulated root into a closed cuvette containing 10% acetylene and then measuring ethylene accumulation measured with time (the closed system assay). Alternatively, 10% acetylene may be passed continuously through a cuvette containing the nodulated root, while ethylene concentration in the effluent gas stream is measured (the open system assay). In the former case, the assay provides only an isolated measurement of nitrogenase activity at a particularly time, while in the latter case taking discrete samples of effluent gas from the cuvette allows a time-course of nitrogenase activity to be measured. Both methods suffer from the fact that in vivo nitrogenase activity is inhibited by exposure of nodulated roots to acetylene. Consequently, the assays often greatly underestimate true activities. Also, the assays provide only a measurement of total nitrogenase activity and cannot be used to measure $N_2$ fixation rate. In addition, the assays require the use of an expensive gas chromatograph, and the use of an explosive acetylene/air mixture that requires very careful handling.

Figure 1:
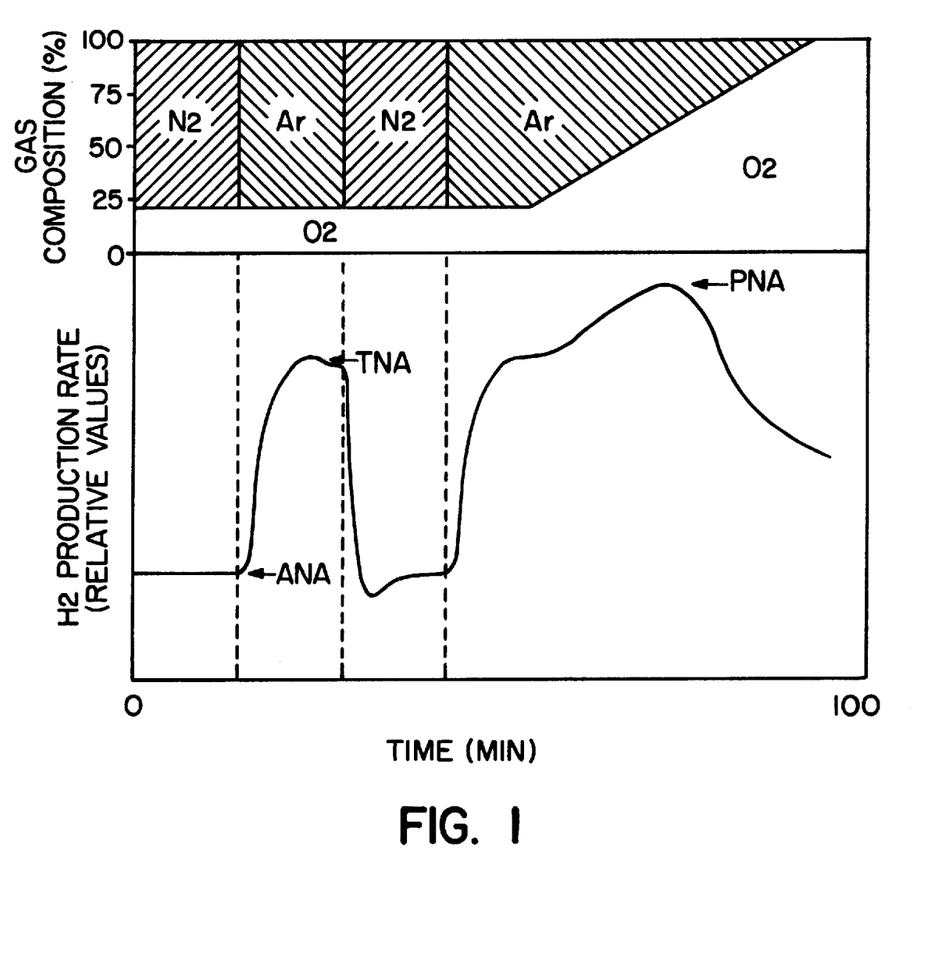
FIG. 1 is a graph illustrating the typical rates of $H_2$ gas production from a nodulated legume root system (Lower Panel) exposed to changes in the gas phase surrounding the roots (Top Panel), where ANA is apparent nitrogenase activity ($H_2$ evolution in $N_2:O_2$), TNA is total nitrogenase activity (peak $H_2$ evolution rate in $Ar:O_2$) and PNA is potential nitrogenase activity (maximum rate of $H_2$ evolution attained in $Ar:O_2$ as $pO_2$ is increased to 100%)..

(d) The $H_2$ evolution assay which depends on the fact that during $N_2$ fixation, the nitrogenase enzyme also reduces protons to $H_2$ gas which is evolved from the nodule. $H_2$ evolution rate may be measured by sealing a nodulated root in a cuvette and measuring the accumulation of $H_2$ in the cuvette with time (the closed system $H_2$ assay), or by passing gas through the cuvette continuously and monitoring $H_2$ concentration in the effluent gas stream (the open system $H_2$ assay). $H_2$ may be monitored in discrete samples of the effluent gas by gas chromatography, or $H_2$ concentration may be monitored continuously using a semiconductor $H_2$ analyzer such as that described by Layzell et al. (Plant Physiol. 582–585, 1984). The rate of $H_2$ evolution in air provides a measurement of apparent nitrogenase activity (ANA) since only a proportion of the electron flow through nitrogenase is used for proton reduction. To measure total nitrogenase activity (TNA), it is necessary to expose nodulated roots to a gas mixture lacking $N_2$, such as an $Ar:O_2$ (80:20) mixture. In the absence of $N_2$, all electron flow is diverted to proton reduction and the rate of $H_2$ evolution from the nodule provides a measure of TNA (FIG. 1). The difference between the rates of $H_2$ evolution in $N_2:O_2$ and in $Ar:O_2$ at a constant $pO_2$ can be used to estimate $N_2$ fixation rate thus:

$$N_2 \text{ Fixation Rate} = (TNA - ANA)/3 \quad \text{Equation 1}$$

A denominator of 3 is used since 3 electron pairs are used in the reduction of $N_2$ compared to 1 electron pair for the reduction of protons to $H_2$ gas.

The measurement of $H_2$ evolution using a $H_2$ analyzer in the open system assay has several advantages over other methods for measuring nitrogenase activity and $N_2$ fixation rate. These include:

The $H_2$ analyzer is extremely sensitive and it is the only instrument which allows continuous, real-time measurement of nitrogenase activity.

The $H_2$ analyzer is the only instrument which allows measurement of ANA, TNA, EAC and $N_2$ fixation rate on the same plant material.

Measurements of ANA and short-term measurements of TNA are not inhibitory to nitrogenase so that measurements can be performed on the same plant material either continuously or intermittently over virtually any experimental period.

The method is not labour intensive and the $H_2$ analyzer is much cheaper than the mass spectrometer required for $^{15}N$ measurements or the gas chromatograph required to measure ethylene production.

Despite these advantages, relatively few researchers use the $H_2$ evolution assay to measure nitrogenase activity. This is because the method has some disadvantages. These include:

The assay can only be used on legume symbioses which lack the enzyme uptake hydrogenase (HUP). This enzyme recycles some or all of the $H_2$ produced by nitrogenase. Although $H_2$ analysis cannot be used to measure nitrogenase activity in HUP$^+$ symbioses, many agriculturally-important symbiosis are HUP$^-$.

Extended exposure of nodulated roots to $Ar:O_2$ causes inhibition of nitrogenase. However, short-term exposures are not inhibitory and repeated assays of TNA can be made on the same plant material.

The output of the $H_2$ analyzer changes with $pO_2$, with differences in water content of the gas stream and with the nature of the balance gas ($N_2$ or Ar). The analyzer is, therefore, difficult and time-consuming to calibrate.

The acetylene reduction assay, and current methods of the $H_2$ assay, require that plants are sealed in their growth pots to allow nitrogenase end-products to accumulate before analysis (closed system assays), or to allow nodulated root systems to be flushed with specific gas mixtures (open system assays). The procedures for both assays are time-consuming, and at least 5 minutes is required before stable measurements can be obtained. Also, the pots must be unsealed after the assays are completed if further growth and development of the plant is to be studied. This increases the time required to conduct the measurements, which limits the number of plants that can be assayed within a working day. A further limitation to the use of both the acetylene and $H_2$ assays is that they require the use of sophisticated instrumentation, and the supply of specific gas mixtures to the material being studied. As a result the assays can only be conducted in laboratories within research institutions, or in mobile laboratories constructed in the field.

These limitations of the acetylene and $H_2$ assays make them unsuitable for the large scale screening of plants that is needed to identify legumes with specific $N_2$-fixing characteristics. At present, much of the research in the field of $N_2$ fixation involves genetic manipulation of legumes, and assessment of the effects of such manipulation on nitrogenase activity. This approach requires the growth of large populations of genetically altered plants (usually in a greenhouse) and assessment of their nitrogenase activities under various environmental conditions. To make appropriate statistical analyses of the data, the plants must be screened at the same stage of development and, as near as is possible, at the same time of day. It should be apparent, therefore, that there is need for a rapid method of nitrogenase activity analysis that can be performed in a greenhouse setting.

OBJECT OF THE INVENTION

It is an object of the invention to provide a portable instrument by which nitrogenase activity can be measured rapidly in $H_2$-producing legumes by sampling $H_2$ from the medium in which the plants are grown without the necessity for sealing the plants within their growth pots.

Another object of the invention is to provide a method for measuring nitrogenase activity in legumes by sampling $H_2$ from the growth medium thereof.

BRIEF STATEMENT OF INVENTION

By one aspect of this invention there is provided an apparatus for measuring nitrogenase activity of a hydrogen-evolving, nitrogen-fixing plant growing in a container containing a porous growth medium which does not oxidize hydrogen, comprising:

means for sampling gas containing hydrogen at the surface of said medium at a rate approximately equivalent to the rate of hydrogen diffusion from said medium;

a hydrogen sensor;

flow path means for supplying said hydrogen-containing gas sample to said hydrogen sensor;

means for drying said sample in said flow path means;

means for measuring flow rate in said flow path means;

means for monitoring concentration of hydrogen in said flow path, and determining nitrogenase activity therefrom.

By another aspect of this invention there is provided a method for rapid measurement of nitrogenase activity of a hydrogen-evolving, nitrogen-fixing plant growing in a container containing a porous growth medium which does not oxidize hydrogen comprising:

sampling gas containing hydrogen at the surface of said medium and adjacent said plant, at a rate approximately equivalent to the rate of hydrogen diffusion from said medium;

passing said hydrogen-containing gas sample through a hydrogen sensor and determining therefrom nitrogenase activity of said plant.

DETAILED DESCRIPTION OF PREFERRED EMBODIMENTS

Figure 2:
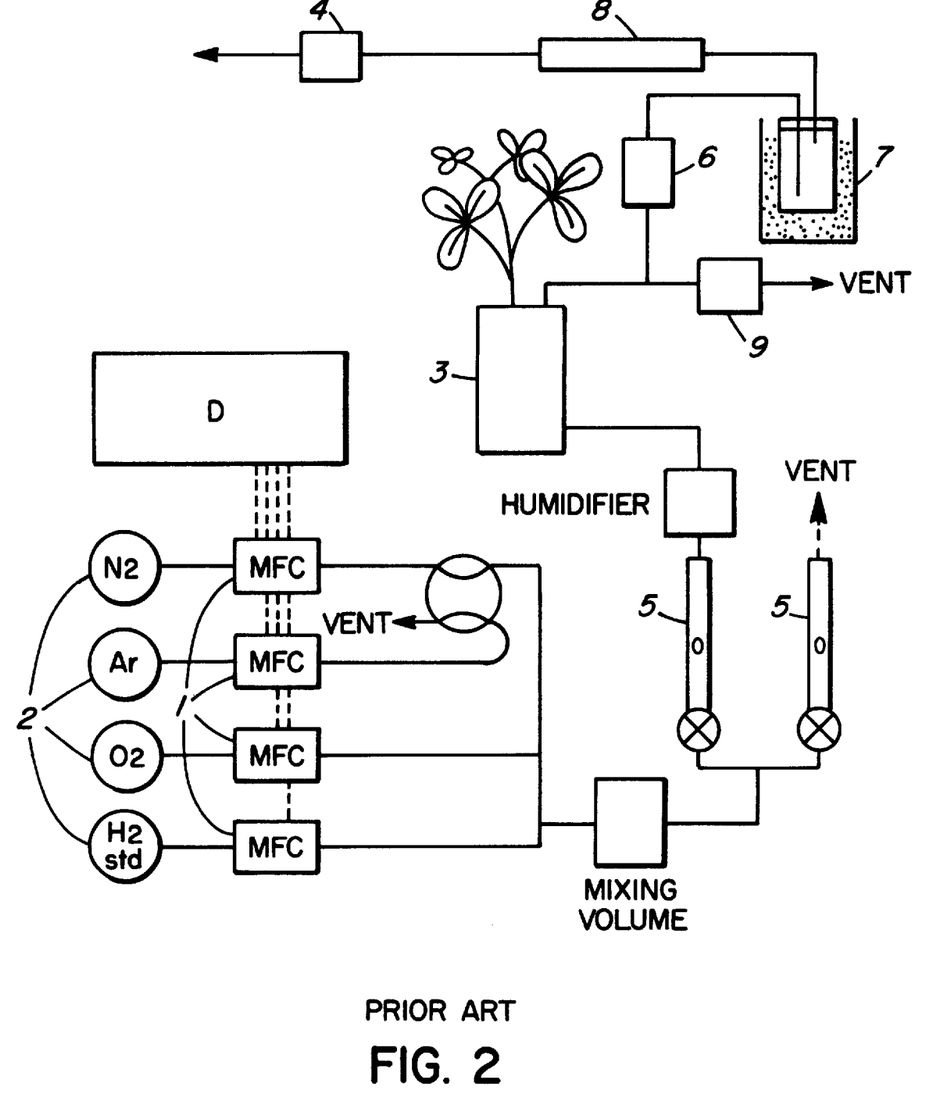
FIG. 2 is a schematic diagram of a prior art open gas exchange system for measuring nitrogenase activity by monitoring $H_2$ evolution from $N_2$-fixing plant material maintained in a sealed cuvette according to the prior art.

A typical method by which nitrogenase activity is currently measured in the laboratory is illustrated in FIG. 2. Electronic mass flow controllers 1 are used to mix gases from tanks 2 and produce any desired gas mixture for supply to a nodulated root system enclosed in a cuvette 3 and from there to a $H_2$ analyzer 4 via an ice bath 7 and a magnesium perchlorate column 8 required for drying the gas. The flow rate of the gas from the mass flow controllers to the cuvette is controlled by needle valves associated with a variable area flow meter 5, and the flow rate to the $H_2$ analyzer is controlled by a pump 6. Excess gas is vented and the $pO_2$ of the gas flushing through the system is monitored by an $O_2$ electrode 9.

For calibration of the $H_2$ analyzer 4 the cuvette 3 would not contain any plant material or would be detached from the system. Gas mixing is controlled by a computer D which both monitors and regulates the outputs from the mass flow controllers 1. The computer program has the ability to mix any combination of $H_2$, Ar, $O_2$ and to alter the proportion of each gas in a mixture either immediately or gradually, and in a linear manner, with time. During calibration, the operator would select a $pH_2$ in $N_2:O_2$ at a known $pO_2$ and monitor the output of the $H_2$ analyzer using either computer D or chart recorder means. When the output is stable, the $PO_2$ can be changed linearly with time between the desired limits and the $H_2$ analyzer output monitored simultaneously. The procedure would then be repeated at a range of $pH_2$ values in $N_2:O_2$. Subsequently, the entire procedure would be repeated with Ar, instead of $N_2$, as the balance gas.

Figure 3A:
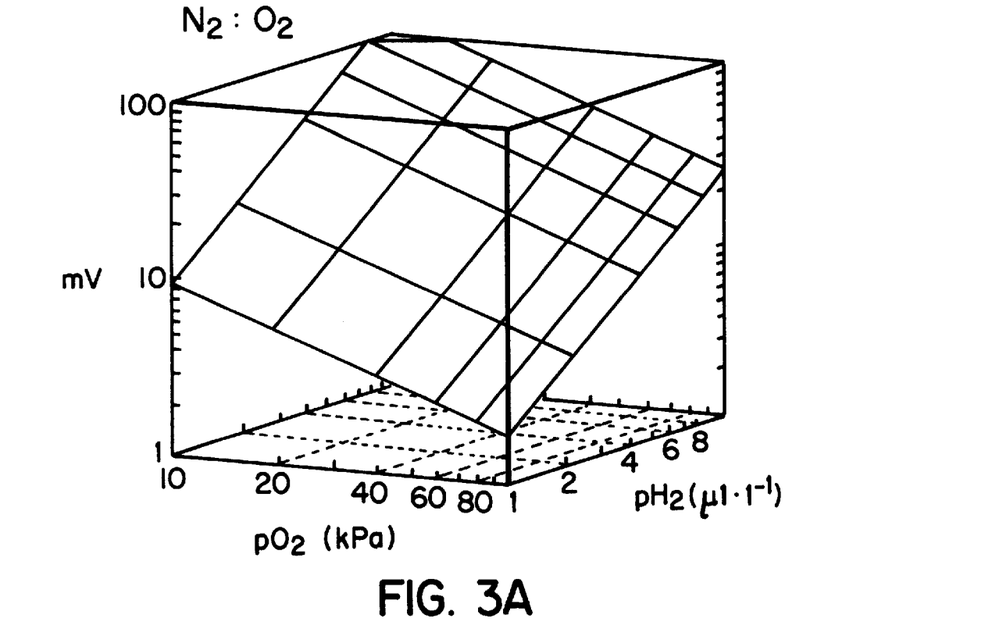
FIGS. 3A and 3B are block diagrams illustrating the relationship between the voltage outputs of the $H_2$ analyzer and the $pH_2$ and $pO_2$ of the gas passing through the $H_2$ analyzer when the values for voltage output, $pH_2$ and $pO_2$ are expressed as natural logs, and the balance of the gas is either $N_2$ (FIG. 3A) or Ar (FIG. 3B).
Figure 3B:
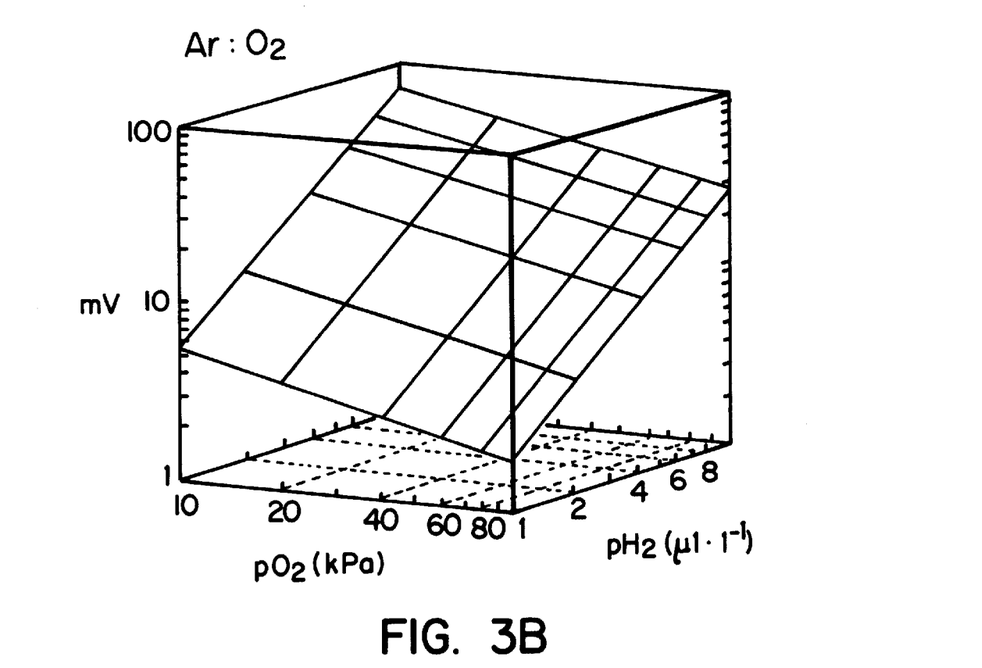

Two sets of data would be collected during the calibration of the $H_2$ analyser; one for $N_2:O_2$ gas mixtures and one for $Ar:O_2$ gas mixtures. Each data set would consist of 3 columns of numbers relating $pH_2$ to the voltage output of the $H_2$ analyzer at a range of $pO_2$. Since the voltage output of the $H_2$ analyzer is not linear with respect to $pH_2$ or $pO_2$, the relationship between voltage, $pH_2$ and $pO_2$ is linearized by converting the values to their natural logs. A multiple linear regression is then performed on each data set to calculate the equation of the plane which defines the relationship between ln (volts), ln ($pH_2$) and ln ($pO_2$) (see FIG. 3). The equation of each plane has the form:

$$ln\ (pH_2) = [ln\ (Volts)*a] + [ln\ (pO_2)*b] + c. \qquad \text{Equation 2}$$

where a and b are coefficients from the multiple linear regression and c is the constant. The calibration planes for a specific $H_2$ analyser are not constant, but change gradually with time. Also, if the $H_2$ sensor within the analyser is exposed to very high $H_2$ levels (e.g. over 1000 ppm), or to 100% $O_2$ or zero $O_2$ for extended periods its calibration changes markedly. For this reason, the calibration must be checked on a daily basis, and a full calibration in $Ar:O_2$ and $N_2:O_2$ must be performed frequently.

To measure nitrogenase activity in a nodulated root system, or other $N_2$-fixing system, the plant material is sealed in the cuvette and $N_2:O_2$ at a known $pO_2$ is flushed through the system at a known flow rate. $H_2$ evolution from the plant material is monitored as the voltage output from the $H_2$ analyzer until steady conditions are attained (FIG. 1). The $H_2$ production rate at this point is termed ANA. To measure TNA, the gas stream is switched from $N_2:O_2$ to $Ar:O_2$ at the same $pO_2$ and the voltage output from the $H_2$ analyzer is monitored until a maximum value is attained (FIG. 1). This maximum $H_2$ production rate represented by this voltage value is termed TNA. Long term exposure to $Ar:O_2$ leads to nitrogenase inhibition, so the gas stream must be switched back to $N_2:O_2$ if this inhibition is to be avoided. Alternatively, after the maximum voltage output is attained in $Ar:O_2$ at the initial $pO_2$, the computerized gas mixing system can be used to increase $pO_2$ in Ar gradually at a defined rate, and the voltage output from the $H_2$ analyzer monitored continuously. Such an experiment may determine the maximum potential nitrogenase activity (PNA) of the plant material since it has been shown that $O_2$ concentration limits nitrogenase activity under normal conditions and severely limits this activity under many adverse conditions.

After an experiment of the type summarized in FIG. 1, the user must calculate ANA, TNA, and PNA by converting the $H_2$ analyzer output voltages measured at the appropriate points in the experiment to values of $pH_2$ using the form of Equation 2 derived in $N_2:O_2$ or $Ar:O_2$ atmospheres. This requires that the $pO_2$ at each point in the experiment is also known. The $pH_2$ calculated from this equation can be converted to a rate of $H_2$ production from the plant material using the following equation:

$$\mu mole\ H_2/hr = (pH_2 * 0.164 * FR * P)/(R*T) \qquad \text{Equation 3}$$

where $pH_2$ is in units of ppm, FR=gas flow rate through the cuvette in mL/min, R=gas constant of 22.4136 L/mol at 273K and 100 kPa pressure, T=temperature in K, and P=ambient pressure in kPa. Values of ANA, TNA and PNA can then be used to calculate $N_2$ fixation rate, EAC and $OLC_N$ according to Equations 1, 2 and 3.

Morgan Scientific Inc. of Haverhill, Mass. are currently marketing a Nitrogenase Activity Analysis System (NAAS), that integrates the components shown in FIG. 2 into a single instrument (Morgan Scientific Brochure 1995). The NAAS is capable of measuring nitrogenase activity automatically, but it is a laboratory-based instrument, and still requires that the user seal the plant under investigation into its growth pot for flow-through gas exchange measurements. It is not suitable for rapid screening of large populations of plants in a greenhouse.

Portable $H_2$ Analyser for Rapid Screening

Prior art methods of measuring nitrogenase activity by $H_2$ analysis were designed for physiological investigations in which activity is to be observed in real time under changing environmental conditions. These methods require the use of elaborate gas mixing devices, and complex calibration procedures for determining absolute nitrogenase activities. Also, the pot in which a plant is grown must be sealed before measurements are made. The flow rate of gas through the pot determines the concentration of plant-derived gases in the analysis gas stream, and the natural atmospheric conditions under which the plant is grown are therefore disturbed. This method of open flow gas analysis is a standard procedure for measuring not only nitrogenase activity in legumes, but physiological processes such as photosynthesis in leaves and respiration in animals.

For rapid measurements of physiological processes by gas exchange, standard methods of open flow gas analysis are not appropriate. In particular, the time-consuming task of sealing and unsealing cuvettes containing the material under study must be avoided. For example, when screening large populations of plants for variations in nitrogenase activity the time constraints involved in prior art methods of $H_2$ analysis would allow only a small proportion of the population to be screened in a single working day. In these investigations it is often more important to rapidly identify plants within a population that have nitrogenase activities significantly higher or lower than the rest of the population. For this purpose, only apparent nitrogenase activity (ANA) need be determined, which requires measurement of $H_2$ evolution in air alone. Therefore, the gas mixing components, and much of the calibration procedures, of the prior art are unnecessary. However, until development of the portable $H_2$ analyzer, described below, pots still had to be sealed within their growth pots before measurements could be made. The new instrument circumvents this limitation and allows measurements of ANA to be conducted in a fraction of the time required for standard open flow ANA measurements. A new calibration procedure has also been developed to make the ANA measurements quantitative, and portability of the instrument allows for screening of large plant populations outside of the laboratory.

The method of measuring nitrogenase activity using the portable $H_2$ analyzer is very different from that using open-flow gas exchange analysis. The portable $H_2$ analyzer takes a sample of gas directly from the surface of the planting medium in which the legume is grown, without the need for sealing the pot, and the concentration of $H_2$ in this sample is used to estimate relative, or absolute, apparent nitrogenase activity. An essential feature of the instrument is that the gas sampling procedure causes minimal disturbance of the normal diffusion of $H_2$ from the planting medium. Unlike standard open-flow gas exchange measurements which disturb, and then create, new steady state gas concentrations in the pot, the portable $H_2$ analyzer relies on the conditions remaining stable during the sampling period. In these circumstances, for plants grown in similar pots containing a similar planting medium, the $H_2$ concentration in the sampled gas will be directly proportional to the nitrogenase activity of the nodulated root. The method used to sample gas while maintaining steady state gas concentration in the sampling medium is described below.

Figure 4:
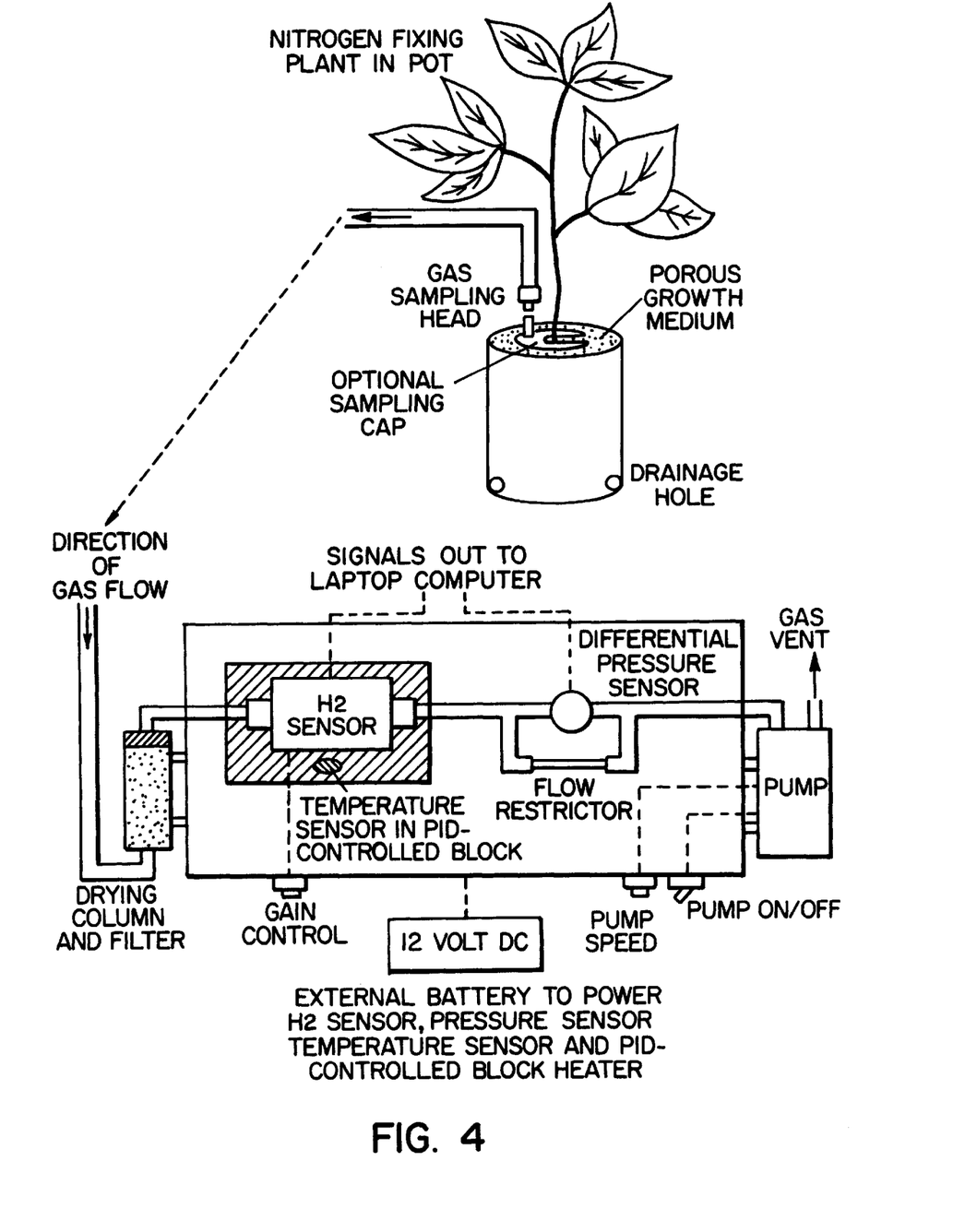
FIG. 4 is a schematic diagram of the embodiment of an apparatus according to the present invention.

A preferred embodiment of the portable $H_2$ analyzer is shown in FIG. 4. A pump (Brey Model GO1 ASF Industries, Norcross, Ga.) pulls gas into the instrument through an external column filled with a magnesium perchlorate drying agent. The dry gas passes through a filter to remove particulate matter, and then through a $H_2$ sensor (Model 822, Figaro Engineering Inc., Osaka, Japan) enclosed within a temperature-insulated block. The sensitivity of the $H_2$ sensor alters with temperature, and since the instrument may be used in the field or greenhouse where environmental conditions vary, it is essential to maintain a constant sensor temperature. This is achieved by heating the sensor with a PID-controlled heating device. A sensor monitors the temperature of the insulated block and the signal from this sensor feeds into the PID controller to maintain a constant temperature. The flow rate of gas through the instrument is monitored by measuring the pressure drop across a flow restrictor in the gas line using a differential pressure sensor (Model MPX10DP, Motorola Corporation, USA). Flow rate can be altered by varying the pump speed using a potentiometer. Outputs from the $H_2$ and differential pressure sensors are monitored, preferentially, by a lap-top computer, although a 2 channel analog recording device may be used. Power for the pump, heater and the sensors is supplied by an external 12 V battery. Mains power may also be used in conjunction with an appropriate 12 V DC transformer.

The gas sampling head of the instrument consists of an $\frac{1}{8}$ inch (i.d.) LUER® fitting attached to flexible $\frac{1}{8}$ inch (i.d.) Tygong tubing. The sampling head may be used to "sniff" gas from any source that generates $H_2$, but when it is used for measurement of nitrogenase activity in legumes, the head is attached to a novel sampling cap that fits on the surface of the planting medium. The sampling cap is a plastic disc with a slot for accommodating the stem of the plant, and a lip 0.5 cm deep around its perimeter which is pushed into the planting medium before sampling. The cap allows $H_2$ to be sampled from a greater area of the planting medium than if the sampling head alone were used. This is important because $H_2$ evolution from the planting medium is not uniform but is often greatest closer to the stem, since the crown region of the root, at the root-stem junction, has the greatest concentration of $H_2$-evolving nodules. Use of the sampling cap therefore reduces the variation that would occur in measurements if gas samples were collected over a smaller surface area of the planting medium.

Figure 5:
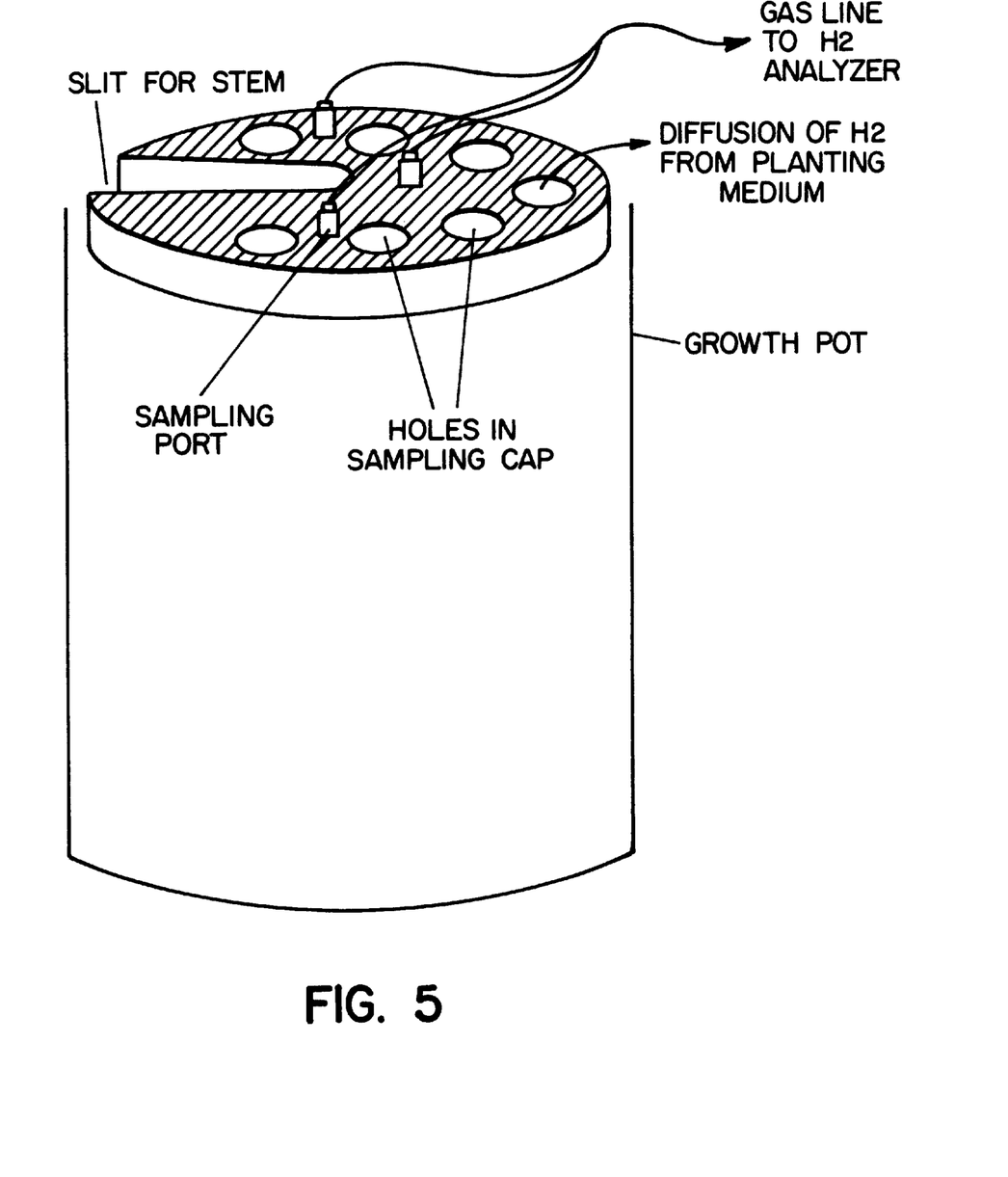
FIG. 5 shows an alternative embodiment of the soil gas sampling cap.

For reasons described above, it is essential that the normal diffusion characteristics of $H_2$ from the planting medium are disturbed as little as possible during sampling. Mathematical models of $H_2$ diffusion in a porous medium (such as the silica sand that it used typically for the growth of legumes used in gas exchange studies) have shown that when plants are grown in gas-impermeable pots open to the atmosphere, flow rate of $H_2$ out of the pots due to diffusion is equivalent to 50–100 ml/min at 20° C. Therefore, gas cannot be sampled from the surface of the medium at a greater flow rate without depleting $H_2$ at the surface and altering steady state conditions. However, covering the surface of the sampling medium with the sampling cap may also disturb the diffusion characteristics of $H_2$ and lead to erroneous results. Mathematical modeling has shown that a balance must be struck between the need to sample $H_2$ from a large surface area of the planting medium, and the need to prevent changes in $H_2$ diffusion. The models predict that the sampling cap should cover not more than 60% of the surface of the planting medium, allowing $H_2$ to diffuse freely from the remaining surface during the sampling period. In one embodiment of the cap, as shown in FIG. 4, the cap is a solid disc of plastic with a slit that accommodates the stem of the plant, and with a single gas outlet port connected to the $H_2$ analyzer. In an alternative embodiment (FIG. 5), the disc covers almost the entire surface of the planting medium, but contains holes accounting for 40% of the area of the medium, through which $H_2$ diffuses to the atmosphere. In this embodiment, there may be several gas outlet ports through which $H_2$ is sampled, these combining into a single gas stream that enters the analyzer. Using either embodiment of the sampling cap, at a sampling flow rate of 30 ml/min, the steady state $H_2$ concentration within the sample can be measured within 45 seconds, during which time $H_2$ diffusion from the soil remains stable.

It should be noted that the sampling cap is not designed to capture all the $H_2$ evolved from the nodulated root, and its function is quite different from soil gas sampling devices that are available commercially. For example LI-COR Inc. (Lincoln, Nebr.) market a soil respiration chamber (Model 6000-09), that incorporates a soil sampling collar for measuring $CO_2$ flux over a specific area of soil surface, by sampling all the gas exchanged over that surface. The sampling cap used with the $H_2$ analyzer collects only a portion of the total $H_2$ evolved from the surface of the planting medium, and the cap may differ in dimension depending on the size of the pot in which it is used. For a given population of plants grown in pots with the same dimensions, use of a standard sampling cap increases the accuracy of relative measurements of nitrogenase activity, or, if the $H_2$ analyzer is calibrated as described below, increases accuracy of quantitative measurements of nitrogenase activity.

Calibration and Use of the Portable $H_2$ Analyzer

Qualitative Measurements of Nitrogenase Activity

Figure 6:
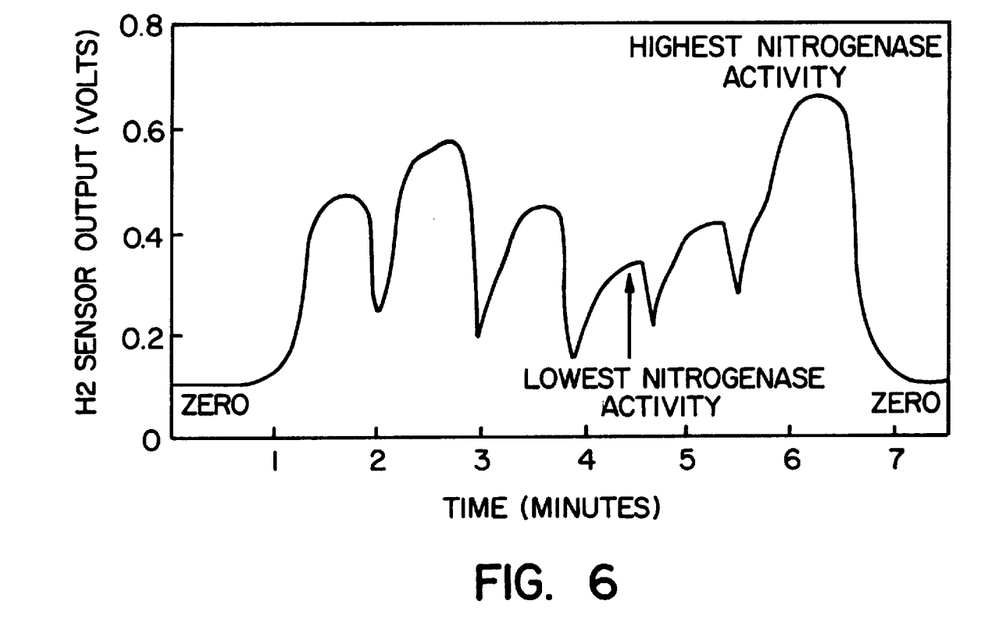
FIG. 6 shows typical data from the portable $H_2$ analyzer when it is used to measure $H_2$ production from 6 legume plants in sequence. Highest and lowest relative nitrogenase activities detected by the analyzer are shown.

For qualitative measurements of nitrogenase activity, in which activity is to be compared among individual plants in a population, calibration of the $H_2$ sensor is not essential. To make these measurements of nitrogenase activity the analyzer pump is set at a constant flow rate (typically 30 ml/min), and the sampling head is attached to the cap. Normal air is sampled to obtain a zero reading from the $H_2$ sensor, and then the cap is placed around the stem of the plant as shown in FIG. 4. Gas from the surface of the growth medium is sampled until a stable output from the $H_2$ sensor is observed (usually within 45 seconds). The procedure is then repeated on the next plant. Since the voltage output from the $H_2$ sensor is proportional to the amount of $H_2$ evolved from the plant during $N_2$ fixation, plants can be screened for high or low nitrogenase activities on the basis of relative voltage measurements alone. An example of a set of relative nitrogenase measurements made on a population of lupin plants is shown in FIG. 6.

It is important when using this method to ensure that plants are grown in pots with uniform dimensions and in the same planting medium, since pot shape and size, and the diffusion characteristics of gases through different media, can affect the efficiency of $H_2$ capture by the sampling cap. The planting medium must be free-draining so that water does not restrict $H_2$ diffusion, and a medium with the porosity of coarse silica sand (Grade 16) is recommended. Even in such a medium, measurements should not be taken within 60 minutes of watering the pot. Soil should not be used as a planting medium for two reasons. First, it retains water, and second it contains micro-organism that have the capacity to oxidize $H_2$. The presence of $H_2$-oxidizing microorganisms in the planting medium will lead to underestimates of nitrogenase activity, and it is recommended that all planting media should be sterilized before cultivation of the legumes.

As described above, it is essential to set a flow rate through the $H_2$ sensor that samples the gas from the surface of the planting medium without depleting the $H_2$ concentration at the sampling point. Although a flow rate of 30 ml/min is recommended, other flow rates may tested by observing the response of the $H_2$ sensor after the sampling cap is placed on the soil surface. If sensor output increases gradually to a steady state, it is unlikely that $H_2$ is being depleted at the surface of the growth medium. If, however, the output peaks and then declines to a steady state, $H_2$ depletion is indicated and a lower flow rate must be used.

Quantitative Measurements of Nitrogenase Activity.

To make quantitative measurements of nitrogenase activity it is essential that the $H_2$ sensor is calibrated. This is achieved by pumping gases containing known concentrations of $H_2$ through the analyzer while monitoring $H_2$ sensor output. Hydrogen must be mixed with a balance gas of similar composition to the gas (usually air) present in the rhizosphere of the pots in which the test plants are grown. Individual calibration gases may be purchased from gas supply companies, may be mixed using precision gas mixing pumps (e.g. Wosthoff pumps, Calibrated Instruments Inc., Hawthorne, N.Y.) or may be generated by an electrolytic $H_2$ generating device designed specifically for $H_2$ analyzer calibration (NAAS Calibrator, Morgan Scientific, Haverhill, Mass.). After this stage of the calibration, the $H_2$ sensor may be used to determine the concentration (in ppm) of $H_2$ in a flowing gas stream.

Figure 7:
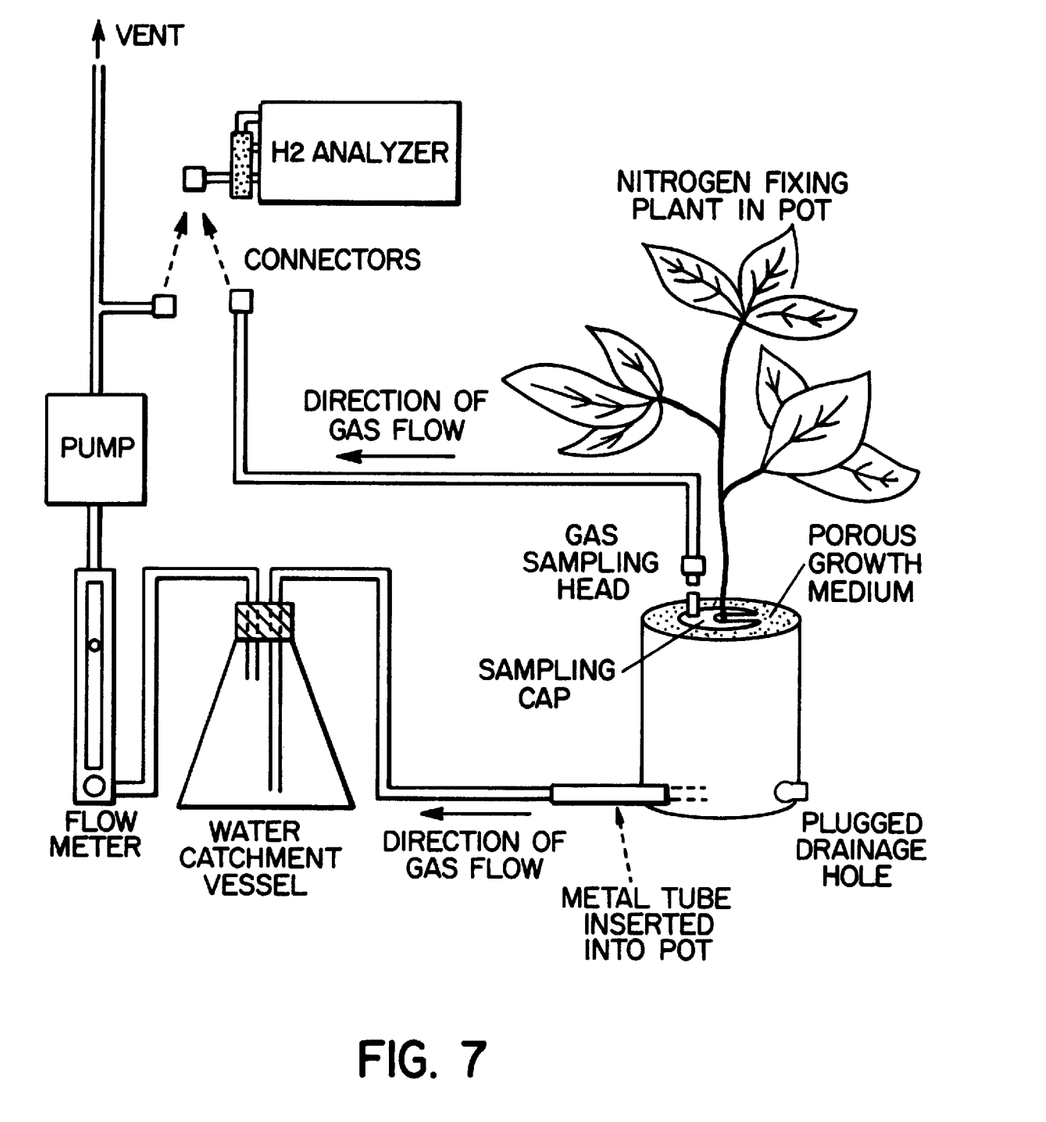
FIG. 7 is a diagram showing the use of the portable $H_2$ analyzer to measure $H_2$ evolution rate (nitrogenase activity) from a $H_2$-producing legume.
Figure 8:
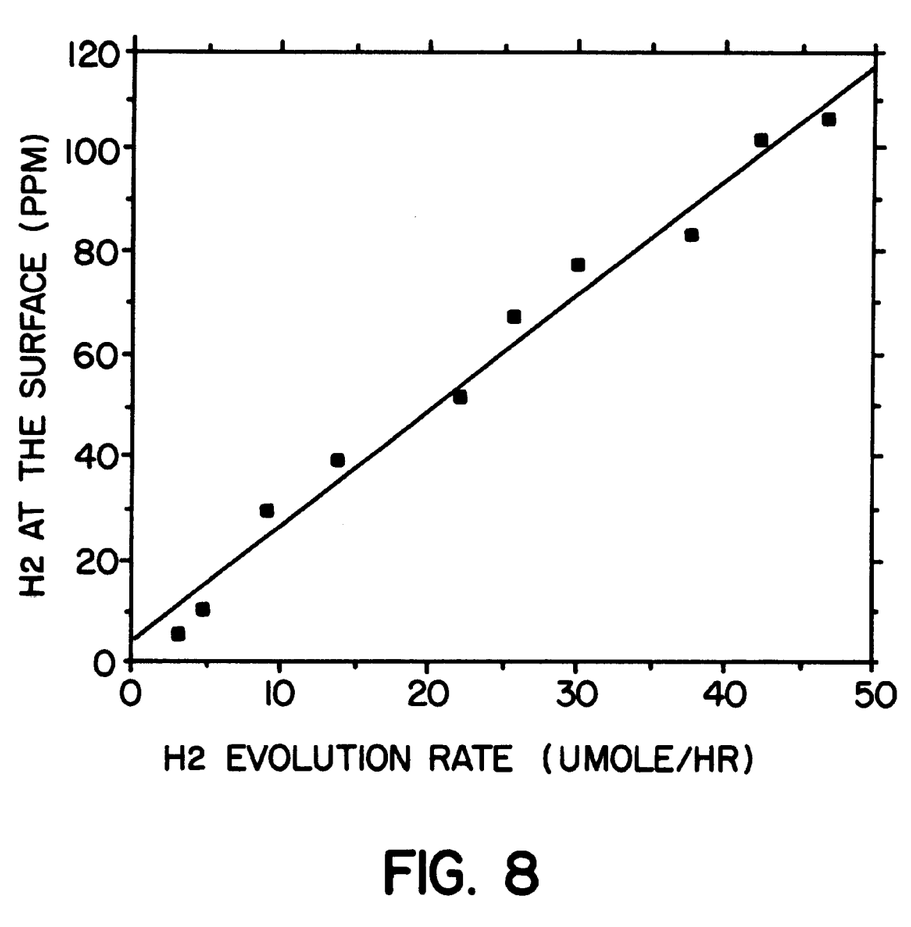
FIG. 8 shows the relationship between $H_2$ concentration measured at the surface of the planting medium in a pot containing a $H_2$-producing legume, and the rate of $H_2$ production (nitrogenase activity) from the nodulated roots of the legume.

The next stage of the calibration procedure occurs as plants are being screened for high and low nitrogenase activities. The sampling cap is placed around the stem of a plant, and the $H_2$ concentration in the gas at the surface of the planting medium is measured using the $H_2$ analyzer. The tubing from the sampling cap is then disconnected from the analyzer, and the sampling cap is removed from the surface of the planting medium. The input of the $H_2$ analyzer is connected to a pump which sucks air from the base of the pot via a metal tube inserted through a drainage hole (FIG. 7). Other drainage holes in the pot are plugged. Outside air is drawn from the top to the bottom of the pot and all the $H_2$ produced by the plant is sampled by the pump. The flow rate at which gas is drawn through the pot is measured by a flow meter, and an in-line water trap prevents nutrient solution from the pot entering the pump. The pump incorporated in the $H_2$ analyzer subsamples the gas from the external pump, and the $H_2$ concentration of the gas stream is measured. The rate of $H_2$ production from the plant can then be calculated from the $H_2$ concentration of the gas stream and the flow rate through the pot according to equation 3 above. This procedure is repeated for several plants which have different $H_2$ concentrations at the surface of the planting medium, so that a relationship is established between the $H_2$ concentration measured by the sampling cap, and the rate of $H_2$ evolution measured by sampling the gas from the base of the pot. This relationship is linear, as shown in FIG. 8. Once the relationship is established it can be used to determine $H_2$ production rate by the nodulated roots from a very quick and simple measurement of surface $H_2$ concentration using the sampling cap. The relationship need not be established prior to screening a large population of plants, but individual plants with various surface $H_2$ concentrations can be selected for rate measurements during the screening process.

Quantitative measurements of $H_2$ evolution rate, as described above, can only be made if the plants being screened are all grown in pots of uniform dimension containing the same planting medium. The cautions regarding the planting medium described above for the qualitative measurements of nitrogenase activity also apply to quantitative measurements.

Voltage outputs from the sensors incorporated in the $H_2$ analyzer are best collected by a lap-top computer via an analog to digital converter, since analog recording devices decrease portability of the instrument and do not allow for easy data manipulation. Several analog to digital converters are available commercially and numerous data acquisition programs exist that can be used for both collection and processing of data. $H_2$ sensor calibrations may be stored within the software to allow for direct conversions of voltage outputs to $H_2$ concentrations, or to rates of $H_2$ production.

Although the principal use of the $H_2$ analyzer is as a portable instrument for rapid screening of nitrogenase activity in large populations of plants, it may also be used in the laboratory for the same purposes as prior art $H_2$ analyzers. ANA and TNA measurements may be made with the instrument as shown in FIG. 4, and measurements of PNA would require only that a gas phase $O_2$ sensor (Model KE-25, Figaro Instruments, Osaka, Japan) be incorporated into the insulated block with the $H_2$ sensor. Full calibration of the $H_2$ sensor in $N_2$:$O_2$ and Ar:$O_2$ gas mixtures, as described under Prior Art, are possible, and calibration data of the type shown in FIG. 3 may be stored in software.

It should also be noted that the portable $H_2$ analyzer may be used for purposes other than measuring nitrogenase activity in legumes. For example, in a medical application it may be used to screen for lactose intolerance, since people who suffer from this intolerance produce $H_2$ gas that can be detected in their breath. The analyzer may also be used in any industrial, scientific, commercial or domestic application in which it is important to monitor the concentration of $H_2$ in the environment. Because the $H_2$ sensor can detect $H_2$ in the part per billion range, the analyzer is of particular importance in any application requiring the detection of very low levels of $H_2$ gas.

We claim:

1. An apparatus for measuring nitrogenase activity of a hydrogen-evolving, nitrogen-fixing plant growing in a container containing a porous growth medium which does not oxidize hydrogen, comprising:

means for sampling gas containing hydrogen at the surface of said medium at a rate approximately equivalent to rate of hydrogen diffusion from said medium;

a hydrogen sensor;

flow path means for supplying said hydrogen-containing gas sample to said hydrogen sensor;

means for drying said sample in said flow path means;

means for measuring flow rate in said flow path means;

means for monitoring concentration of hydrogen in said flow path, and determining nitrogenase activity therefrom.

2. An apparatus as claimed in claim 1 including means for controlling temperature of said hydrogen sensor.

3. An apparatus as claimed in claim 1 including pump means to draw said hydrogen-containing gas through said flow path.

4. An apparatus as claimed in claim 1 wherein said means for sampling hydrogen-containing gas at the surface of said medium comprises a planar member having a dependent rim insertable into said medium, and a slit means to accommodate a stem of said plant; and wherein at least 40% of the surface area of said medium is exposed directly to atmosphere.

5. Apparatus as claimed in claim 4 wherein said planar member includes a plurality of holes.

6. Apparatus as claimed in claim 1 wherein said container is impermeable to hydrogen, and includes at least one drainage hole at the base thereof.

7. Apparatus as claimed in claim 6 wherein said at least one drainage hole has an area of at less than 1% of the surface area of said growth medium.

8. Apparatus as claimed in claim 6 including means to withdraw gas from at least one of said at least one drainage hole.

9. A method for rapid measurement of nitrogenase activity of a hydrogen-evolving, nitrogen-fixing plant growing in a container containing a porous growth medium which does not oxidize hydrogen comprising:

sampling gas containing hydrogen at the surface of said medium at a rate approximately equivalent to the rate of hydrogen diffusion from said medium;

passing said hydrogen-containing gas sample through a hydrogen sensor and determining therefrom nitrogenase activity of said plant.

10. A method as claimed in claim 9, including defining a relationship between said hydrogen concentration at said medium surface and said nitrogenase activity of said plant, by sampling gas at a selected flow rate from a sealed base of said container so that all of the hydrogen produced by said plant is drawn into a gas stream from said sealed base.

11. A method as claimed in claim 10 wherein a subsample of said gas stream from said sealed base is drawn into said hydrogen sensor.

* * * * *